US 6,510,575 B2

(12) United States Patent
Calabrese

(10) Patent No.: US 6,510,575 B2
(45) Date of Patent: Jan. 28, 2003

(54) TOOTHBRUSH

(75) Inventor: Giuseppe Calabrese, Bebington (GB)

(73) Assignee: Unilever Home & Personal Care USA, division of Conopco, Inc., Greenwich, CT (US)

(*) Notice: Subject to any disclaimer, the term of this patent is extended or adjusted under 35 U.S.C. 154(b) by 20 days.

(21) Appl. No.: 09/799,273

(22) Filed: Mar. 5, 2001

(65) Prior Publication Data

US 2001/0020314 A1 Sep. 13, 2001

(30) Foreign Application Priority Data

Mar. 6, 2000 (EP) .............................. 00200800

(51) Int. Cl.[7] .............................. A46B 7/06; A46B 7/08; A61C 17/32; A61C 17/34
(52) U.S. Cl. .............................. 15/22.1; 15/28; D4/101
(58) Field of Search .............................. 15/22.1, 28, 29; D4/101

(56) References Cited

U.S. PATENT DOCUMENTS

| | | | |
|---|---|---|---|
| 5,353,460 A | | 10/1994 | Bauman |
| 5,617,603 A | | 4/1997 | Mei |
| 5,850,655 A | * | 12/1998 | Gocking et al. |
| 5,862,559 A | | 1/1999 | Hunter |
| 5,901,397 A | * | 5/1999 | Hafele et al. |
| 5,996,157 A | * | 12/1999 | Smith |
| 6,237,178 B1 | * | 5/2001 | Krammer et al. |
| 6,360,395 B2 | * | 3/2002 | Blaustein et al. |

FOREIGN PATENT DOCUMENTS

| | | |
|---|---|---|
| WO | 98/37788 | 9/1998 |
| WO | 99/37180 | 7/1999 |

OTHER PUBLICATIONS

European Search Report.

* cited by examiner

Primary Examiner—Terrence R. Till
(74) Attorney, Agent, or Firm—Milton L. Honig

(57) ABSTRACT

Electric toothbrush comprises an oscillating, bristle bearing head which comprises two or more segments which are integral with one another.

8 Claims, 3 Drawing Sheets

TOOTHBRUSH

BACKGROUND OF THE INVENTION

1. Field of the Invention

The present invention relates to an electric toothbrush with an oscillating head.

2. The Related Art

Electric toothbrushes are generally considered to provide a level of cleaning which is at least equal to that obtainable by manual brushes while providing a more convenient mode of operation.

Typical electric toothbrushes comprise a bristle bearing head which oscillates around an oscillating axis, where said axis is usually co-axial with a circular bristle bearing head.

However, some brushes have particular oscillating patterns, such as longitudinally oscillating elements, or they may have multiple brush heads, such as that marketed by Phillips under the tradename 'Plaque Remover®', which comprises a rotating head and an independent, laterally oscillating array of bristles distal to the brush handle.

An object of the present invention is to provide a cheap electric toothbrush, which provides an improved cleaning benefit and is easy and comfortable to use.

SUMMARY OF THE INVENTION

We have found that an electric toothbrush can provide an improvement upon the prior art when the oscillating brush head comprises two or more bristle bearing segments which are integral with one another.

Accordingly, the present invention provides an electric toothbrush comprising an oscillating, bristle bearing head wherein the head includes two or more segments which are integral with one another.

It is to be understood that the term 'head' used with reference to an electric toothbrush means a bristle bearing section and a neck portion connecting the bristle bearing section to the handle.

It is an essential feature of the invention that the segments in the head are integral with one another. By this is meant that they oscillate as a single unit so that a single oscillating means may oscillate the entire head. This in contrast with brushes which have multiple independent oscillating units where a separate mechanism is required to oscillate each bristle bearing member. Accordingly, the term integral is meant to include not just segments which are unitary but also to those which are linked so as to form a single oscillating member.

In a preferred embodiment the oscillating axis of the brush head passes through the brush head. In this way the brush head rotates around the head so that a greater range of motion is effected by the bristles. This is in contrast to a brush head which is merely displaced side to side during oscillation because the axis is remote from the head.

Further to there being any number of segments on such a segmented brush head each segment may be unitary with any of a number of other segments or be linked to any number of other segments by a further material. For example, the brush head may comprise segments which are linked to one another via a material common to both, e.g. a polypropylene base, thereby providing a living hinge. Alternatively, the segments may be separated by a groove or chasm which is comprised solely of the living hinge or it may be partially or solely filled with an elastomeric material.

It is, of course, perfectly feasible for different links to be employed for different segments thereby modifying the oscillating characteristics of the individual segments and the brush head as a whole.

The inclusion of a multi-segmented head can modify the vibrational character of the brush head in such a way as to improve the cleaning of an oscillating brush brush. It is also possible that it may reduce the output required from the motor element, which in turn may make the brush more comfortable to use and reduce the power requirements, thus reducing battery changing frequency.

A conventional brush head comprises hard materials, such as polypropylene or polyacrylonitrile and it may be that the physical dimensions of these materials provide the flexibilty of the head, e.g. the brush head comprises segments which are linked by a hinge comprising a material common with the segments but may also comprise an elastomeric material to supplement the flexibility of the link regions. Alternatively, the elastomer may comprise the link region in its entirety. The inclusion of elastomeric material to the link region of the brush head may extend to surrounding any amount of the brush head. This may reduce the incidence of damage to the users gums and lips as the rubbery elastomer absorbs the vibrations of the motor.

By elastomeric material is meant that the material has some elastic nature. Given that electric toothbrushes vibrate at an extremely high frequency it is anticipated that a high elastic nature is not necessary and a material with a Shore A hardness of less than conventionally used polypropylene is suitable for use in the present invention.

In a preferred embodiment, the rubbery material has a Shore A hardness of less than 100, more preferably less than 80, and especially less than 55. An acceptable minimum Shore A hardness is 13.

Particularly suitable rubbery material -include elastomeric materials such as those described in WO97/20484, the contents which relate to said elastomeric materials are incorporated by reference. Typical of such suitable elastomeric materials include a thermoplastic vlucanate (TPV) consisting of a mixture of polypropylene and EPDM (ethylene propylene diene monomers) which is available as SANTOPRENE (brand), described in U.S. Pat. No. 5,393,79 issued to Halberstadt et at, or VYRAM (brand), another TPV consisting of a mixture of polypropylene and natural rubber, both SANTOPRENE and VYRAM (brands) being elastomers marketed by Advanced Elastomer Systems. Other suitable elastomers include KRATON, a brand of styrene block copolymer (SBC) marketed by Shell, and DYNAFLEX G 2706 (brand), a thermoplastic elastomer marketed by GLS Corporation and which is made with KRATON (brand) polymer. These and other suitable elastomers have, typically, a Shore A hardness of from about 13 to 94, with about 29 being a preferred hardness.

In a preferred embodiment the flexibilty in the head is achieved through the use of a hinge between the segments. Such a living hinge is preferably arranged so as to allow flexing in an axis which is parallel to the oscillating axis. In this way, the oscillation on the brush head around the oscillating axis also directly produces flexing around the living hinge.

It is also envisaged that the head of the brush according to the invention may be replaceable.

In an alternative aspect the invention provides an electric toothbrush with improved sensory benefits. The brush according to the invention provides an improved feel in the oral cavity, especially when the brush comprises a rubbery elastomeric material in the head or neck. This is particularly so when the non-bristle bearing surfaces of the head is significantly covered by an elastomeric material and contacts the buccal lining. This sensory benefit is seen as an important consumer positive.

The electric toothbrush according to the invention provides an improvement over the prior art by the inclusion of a flexible head section. It is thought that the flexible head provides enhanced oscillation/vibration due to its flexible nature or, more specifically, due to the differences in elasticity of the materials/sections comprising the head.

Further embodiments of the invention are now described with reference to the figures.

BRIEF DESCRIPTION OF THE INVENTION

Figure 1:
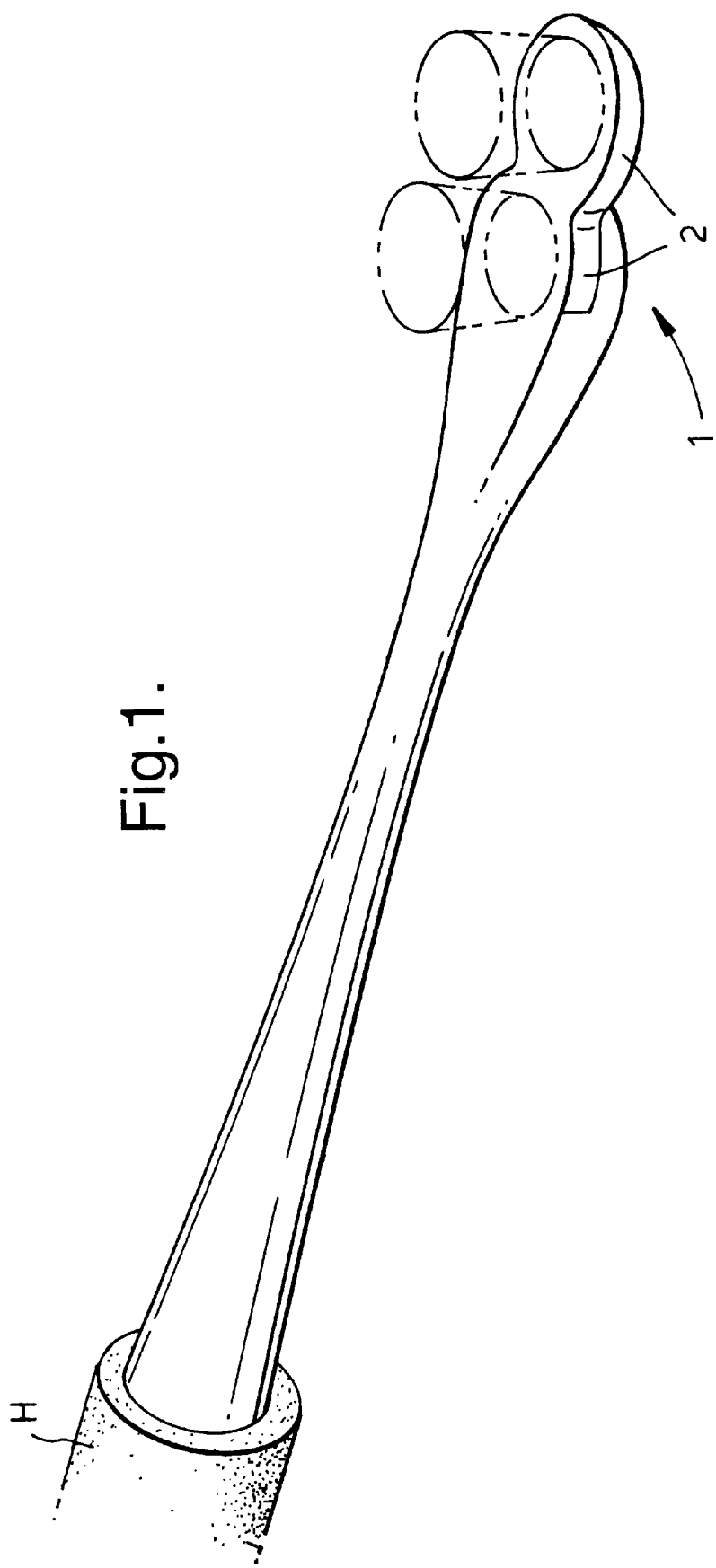
FIG. 1 represents a perspective view of a brush according to the invention.

FIG. 1, shows a brush head (1) comprising two bristle-bearing segments (2). The brush head is attached to a handle (H) which wilt also house the motor.

Figure 2A:
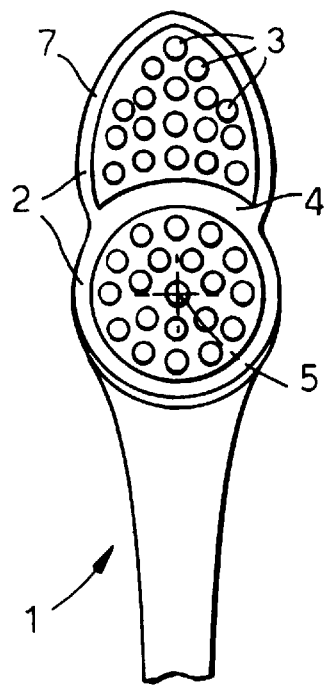
FIG. 2 represents another brush according to the invention and, in detail, the link between the segments.
Figure 2B:
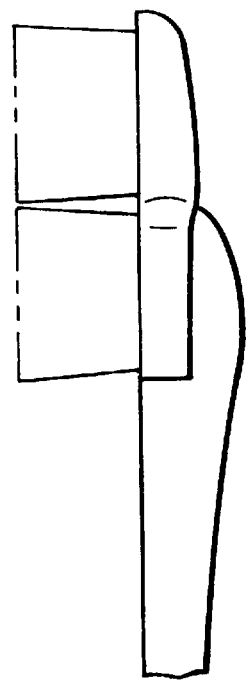
Figure 2C:
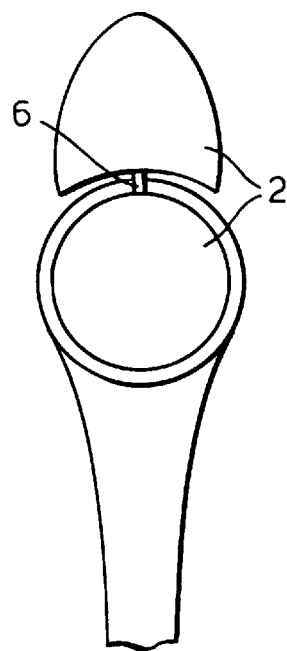
Figure 2D:
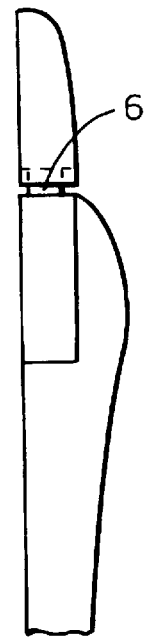

FIG. 2a, shows another brush head (1) comprising two segments (2) each of which bears bristles (3). Both bristle-bearing segments (2) are linked via a flexible link region (4) which comprises, chiefly elastomer material (7). The bristle-bearing segment (2) closest the handle oscillates around an oscillating axis (5) by virtue of a cam means as can be found in conventional electric oscillating toothbrushes. FIG. 2b shows a side view of same brush head. FIG. 2c shows the same brush head without the elastomer surround to illustrate how the living hinge (6) may link to two segments. While it is quite feasible for the living hinge (6) to remain after the elastomer has been moulded around the brush head it may also be removed before the elastomer is provided to produce different flexibility characteristics. FIG. 2d shows a side view of FIG. 2c.

Figure 3A:
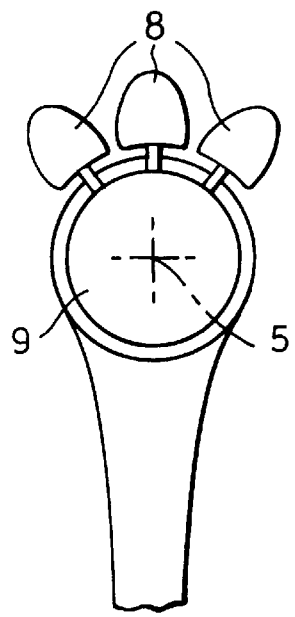
FIG. 3 represents further brush head designs according to the invention.
Figure 3B:
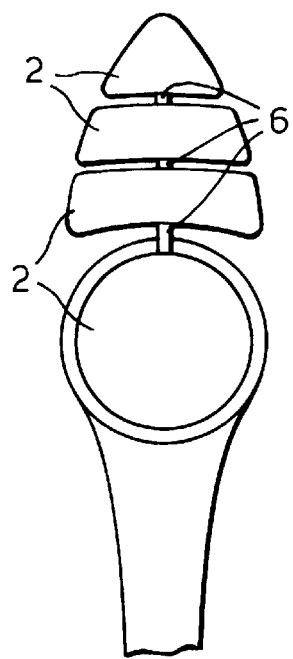
Figure 3C:
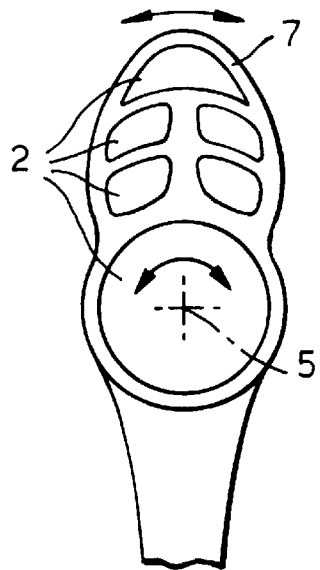

FIG. 3 shows three different embodiments of multihead brushes according to the invention. FIG. 3a shows a brush head comprising four separate segments: three in a tip profile (8) and one main oscillating member (9). While the oscillating member oscillates around oscillating axis (S) the tip segments are also agitated side to side hence providing an additional brushing action. FIG. 3b shows an alternative design whereby the brush head comprises four longitudinally arranged segments each of which bears bristles. Each is attached via a flexible member (6). FIG. 3c shows a further embodiment according to the invention comprising six bristle bearing segments (2) attached to each other at least by elastomeric material (7) and perhaps further by way of a living hinge hidden by said elastomer.

What is claimed is:

1. Electric toothbrush comprising an oscillating, bristle bearing head, characterised in that the head comprises two or more segments which are integral with one another and at least one segment is linked to at least one other segment by a flexible link.

2. Electric toothbrush according to claim 1, characterised in that the head oscillates around an oscillating axis which passes through the head.

3. Electric toothbrush according to claim 1, characterised in that the flexible link comprises a living hinge.

4. Electric toothbrush according to claim 3, characterised in that the living hinge flexes about a flex axis which is substantially parallel to the oscillating axis.

5. Electric toothbrush according to claim 1, characterised in that at least two segments are arranged sequentially from a handle end of the head to a tip end of the head.

6. Electric toothbrush according to claim 1, characterised in that the head oscillates about an oscillating axis which is substantially concentric with a segment.

7. Electric toothbrush comprising an oscillating bristle bearing head, characterised in that the head comprises two or more segments which are integral with one another, at least one segment being separated from at least one other segment by a groove or chasm which is at least partially filled with an elastomeric material.

8. Electric toothbrush according to claim 7, characterised in that the groove or chasm is solely filled with elastomer.

* * * * *